(12) United States Patent
Takenaka et al.

(10) Patent No.: US 9,476,861 B2
(45) Date of Patent: Oct. 25, 2016

(54) ULTRASOUND DIAGNOSTIC DEVICE AND ULTRASOUND PROBE

(71) Applicant: HITACHI ALOKA MEDICAL, LTD., Mitaka-shi, Tokyo (JP)

(72) Inventors: Tomoko Takenaka, Mitaka (JP); Mikio Izumi, Mitaka (JP); Kazunari Ishida, Mitaka (JP)

(73) Assignee: HITACHI, LTD., Tokyo (JP)

( * ) Notice: Subject to any disclaimer, the term of this patent is extended or adjusted under 35 U.S.C. 154(b) by 244 days.

(21) Appl. No.: 14/380,307

(22) PCT Filed: Feb. 21, 2013

(86) PCT No.: PCT/JP2013/054305
§ 371 (c)(1),
(2) Date: Aug. 21, 2014

(87) PCT Pub. No.: WO2013/125626
PCT Pub. Date: Aug. 29, 2013

(65) Prior Publication Data
US 2015/0013462 A1    Jan. 15, 2015

(30) Foreign Application Priority Data
Feb. 23, 2012  (JP) .................................. 2012-036975

(51) Int. Cl.
*G01N 29/44* (2006.01)
*G01N 29/24* (2006.01)
(Continued)

(52) U.S. Cl.
CPC .......... *G01N 29/4463* (2013.01); *B06B 1/0292* (2013.01); *G01N 29/2406* (2013.01); *G01N 29/262* (2013.01); *G01N 29/42* (2013.01); *A61B 8/00* (2013.01); *G01N 2291/045* (2013.01)

(58) Field of Classification Search
CPC ............ B06B 1/0292; G01N 29/2406; G01N 29/42; G01N 29/4463; G01N 29/262; G01N 2291/045; A61B 8/00

USPC .......................................................... 73/602
See application file for complete search history.

(56) References Cited

U.S. PATENT DOCUMENTS 8,333,703 B2 * 12/2012 Kanda ..................... A61B 8/00
                                                                    367/138
9,089,874 B2 *  7/2015 Asafusa ............... A61B 8/4483
(Continued)

FOREIGN PATENT DOCUMENTS

CN          1714754 A     1/2006
CN        101536547 A     9/2009
(Continued)

OTHER PUBLICATIONS

Chinese Office Action dated Oct. 9, 2015, issued in counterpart Chinese Patent Application No. 2013800104428 with English translation (9 pages).

(Continued)

*Primary Examiner* — Jacques M Saint Surin
(74) *Attorney, Agent, or Firm* — Westerman, Hattori, Daniels & Adrian, LLP

(57) ABSTRACT

In order to reduce the variation of transmitting and receiving sensitivity among a plurality of CMUT cells, an ultrasound diagnostic device comprises: a plurality of CMUT cells each having a vibrating membrane that vibrates when ultrasound is transmitted to or received from a subject; an upper electrode and a lower electrode disposed facing each other on mutually opposite sides of each of the CMUT cells to apply a bias voltage to each of the CMUT cells by a bias power supply; and transmitting and receiving correction units for each correcting the voltage supplied from the bias power supply by using a function using at least one parameter of the thickness and resonance frequency of the vibrating membrane of each of the CMUT cells.

15 Claims, 11 Drawing Sheets

(51) Int. Cl.
*G01N 29/26* (2006.01)
*G01N 29/42* (2006.01)
B06B 1/02 (2006.01)
*A61B 8/00* (2006.01)

(56) References Cited

U.S. PATENT DOCUMENTS

| | | |
|---|---|---|
| 2003/0149363 A1 | 8/2003 | Dreschel et al. |
| 2006/0004289 A1 | 1/2006 | Tian et al. |
| 2007/0016020 A1 | 1/2007 | Oshiki et al. |
| 2007/0239008 A1 | 10/2007 | Nakajima et al. |
| 2008/0089181 A1 | 4/2008 | Adachi et al. |
| 2010/0036257 A1 | 2/2010 | Sano et al. |
| 2010/0179430 A1* | 7/2010 | Sano ............... B06B 1/0292 600/459 |
| 2010/0268081 A1 | 10/2010 | Asafusa et al. |
| 2010/0312119 A1 | 12/2010 | Hashiba et al. |
| 2012/0218867 A1* | 8/2012 | Kandori ........... B06B 1/0269 367/95 |
| 2014/0010052 A1* | 1/2014 | Torashima ....... B06B 1/0292 367/181 |

FOREIGN PATENT DOCUMENTS

| | | |
|---|---|---|
| CN | 101888809 A | 11/2010 |
| JP | 2008-118631 A | 5/2008 |
| WO | 2005/032374 A1 | 4/2005 |
| WO | 2009/069281 A1 | 6/2009 |
| WO | 2009/075280 A1 | 6/2009 |

OTHER PUBLICATIONS

International Search Report dated Apr. 2, 2013, issued in corresponding application No. PCT/JP2013/054305.
Written Opinion dated Apr. 2, 2013, issued in corresponding application No. PCT/JP2013/054305.
Notification Concerning Transmittal of International Preliminary Report on Patentability (Chapter I of the Patent Cooperation Treaty)(Forms PCT/IB/326) of International Application No. PCT/JP2013/054305 mailed Sep. 4, 2014 with Forms PCT/IB/373,PCT/IB/338 and PCT/ISA/237; W/English Translation.

* cited by examiner

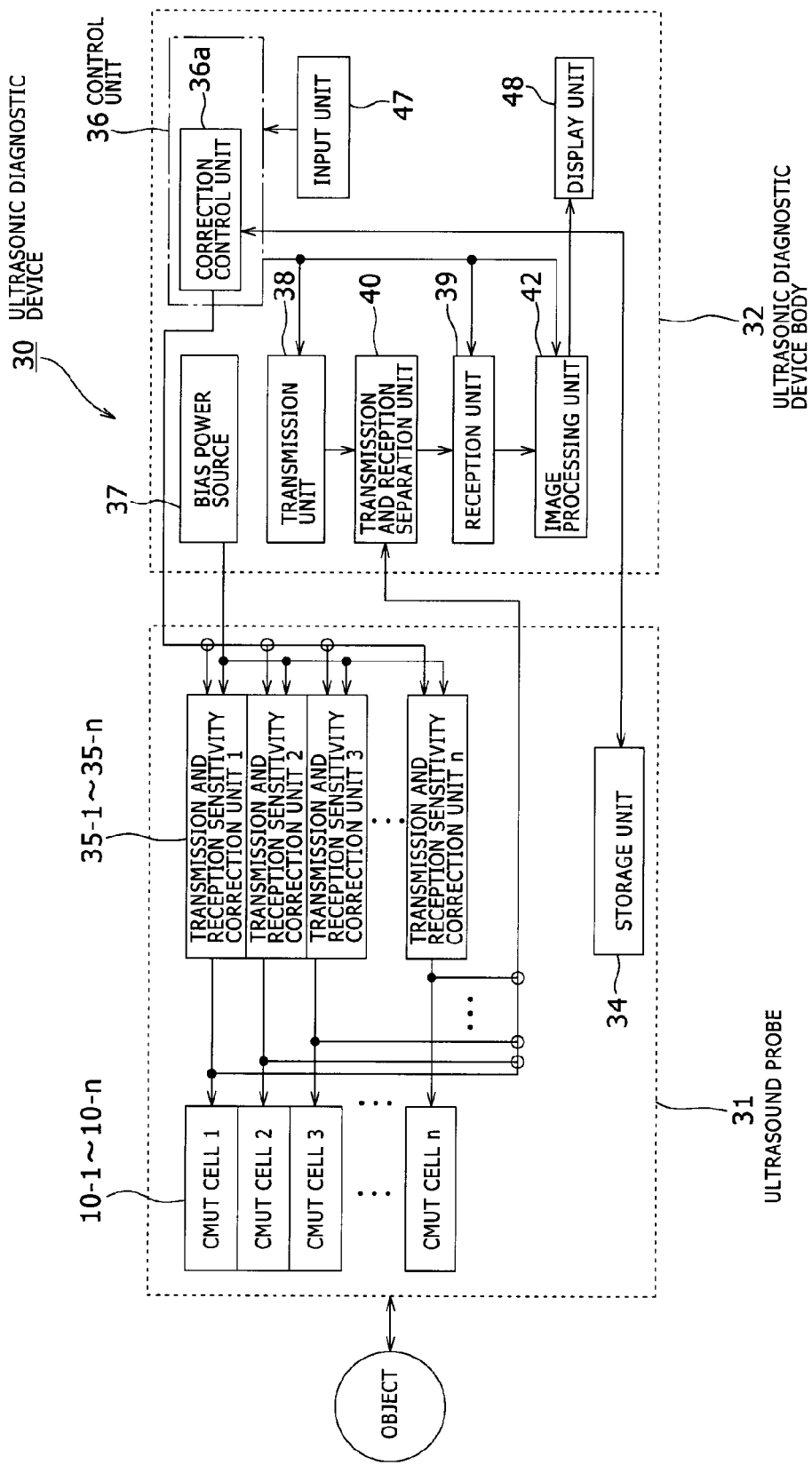
F I G. 2

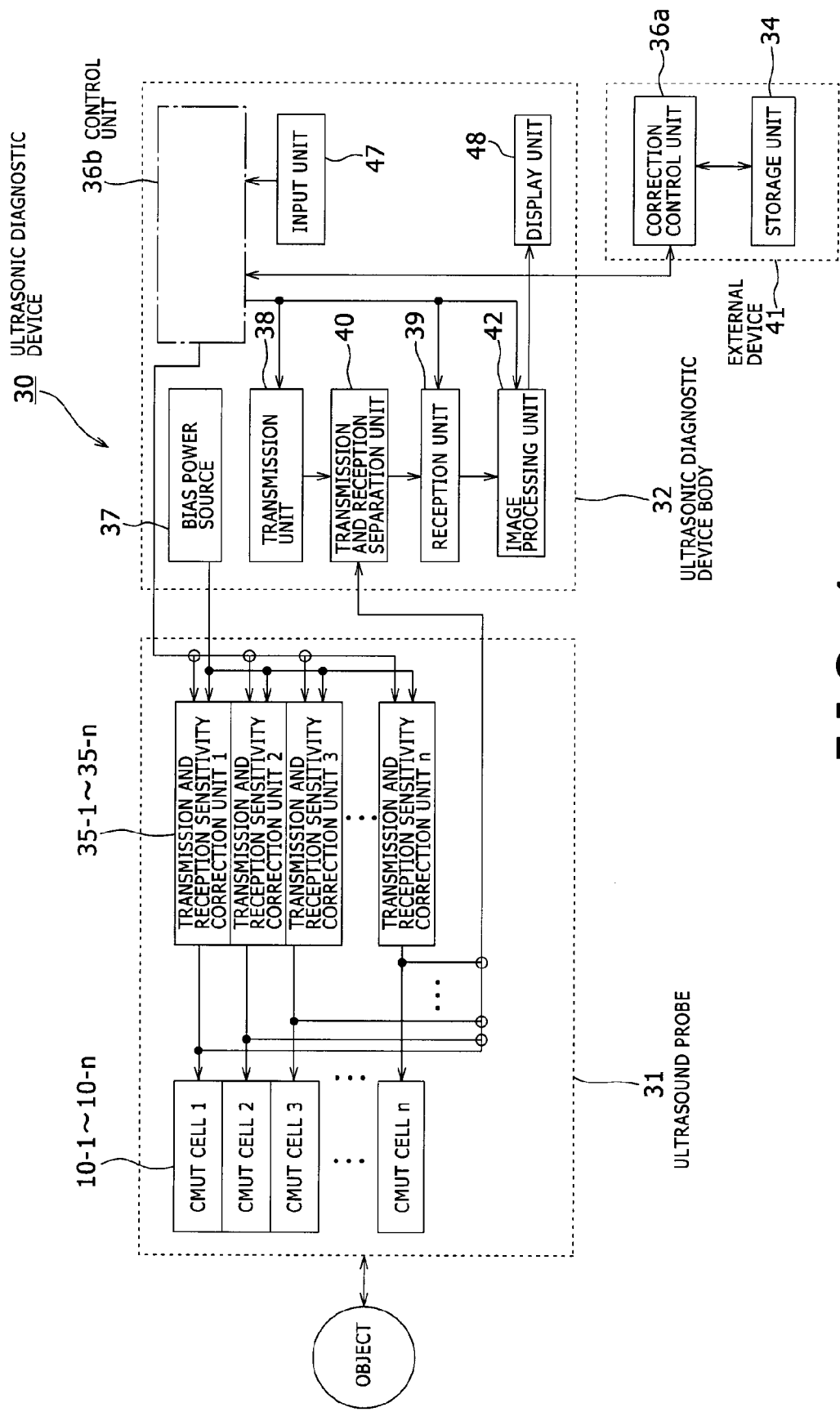
F I G. 4

| CONDITION | GAP THICKNESS g | VIBRATING MEMBRANE THICKNESS t | CORRECTION ACCORDING TO THE INVENTION | NO CORRECTION | COLLAPSE VOLTAGE CORRECTION |
|---|---|---|---|---|---|
| VARIATION | -10 TO +10% | -10 TO +10% | -5.1 TO +4.9% | -19.0 TO +21.0% | -9.1 TO +11.1% |

FIG. 7

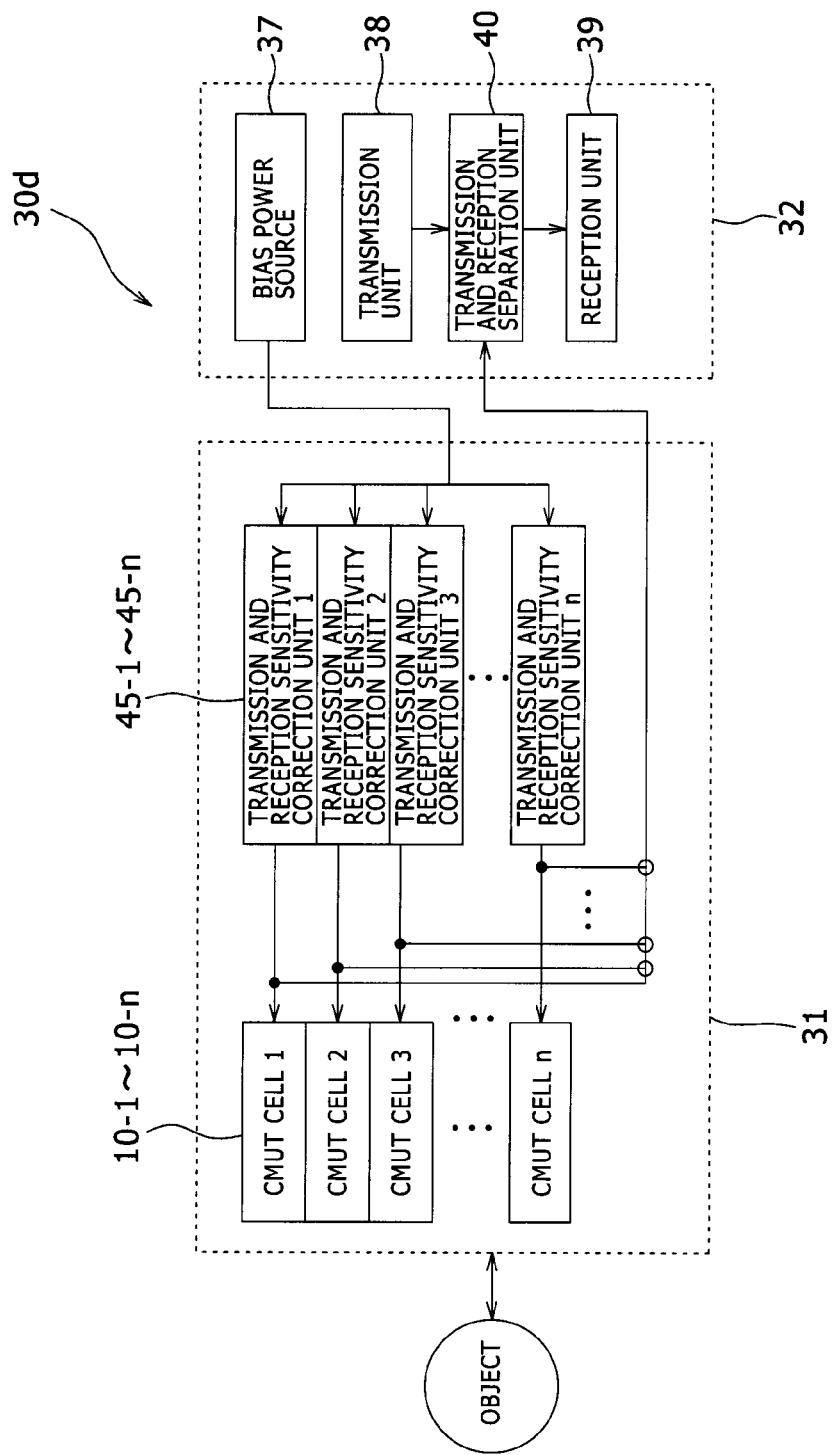
F I G. 8

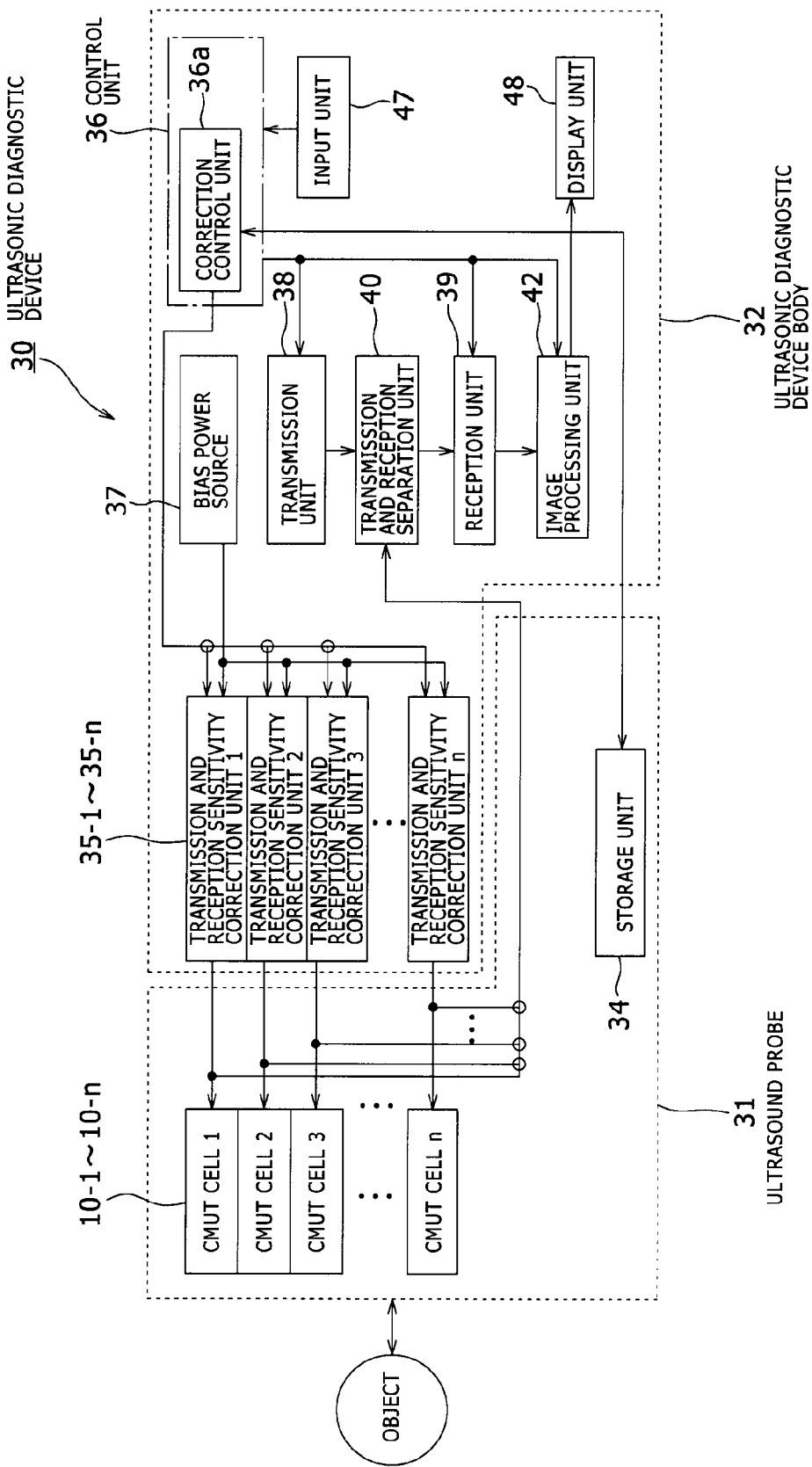
F I G. 12

ULTRASOUND DIAGNOSTIC DEVICE AND ULTRASOUND PROBE

TECHNICAL FIELD

The present invention relates to an ultrasonic diagnostic device and an ultrasound probe capable of suppressing variation in transmission and reception sensitivity of an ultrasound probe particularly using a CMUT.

BACKGROUND ART

An ultrasonic diagnostic device is a device which constructs a diagnostic image by a reflection echo obtained from an ultrasound probe. The ultrasound probe has a transducer which is arranged to perform electroacoustic conversion, converts an electrical signal supplied from the ultrasonic diagnostic device to an ultrasonic wave and transmits the ultrasonic wave to an object, and converts a reflection echo signal generated from the object to a reception signal.

In recent years, an ultrasound probe using a transducer, called a CMUT (Capacitive Micromachined Ultrasound Transducer), has been put into practical use. The CMUT is a capacitive micromachined ultrasound probe which is formed by a semiconductor micromachining process. A CMUT chip which is mounted on an ultrasound probe has a structure in which multiple elements (CMUT cells) each having a drum-like shape of a musical instrument are aggregated, and a portion of each CMUT cell corresponding to the membrane (vibrating membrane) vibrates, thereby performing sound pressure-voltage conversion.

The CMUT has a characteristic in which transmission and reception sensitivity of an ultrasonic wave changes depending on a bias voltage to be applied. However, as is also known, even if the same bias voltage is applied, variation in transmission and reception sensitivity is generated among a plurality of CMUT cells, due to manufacturing variation or residual stress.

In the ultrasonic diagnostic device of the related art, in order to correct variation in transmission and reception sensitivity, an ultrasonic output signal or electrostatic capacitance of each of the CMUT cells is measured, and a corrected bias voltage is applied to each of the CMUT cells (for example, see Patent Literature 1).

CITATION LIST

Patent Literature

Patent Literature 1: International Publication No. 2005/032374

SUMMARY OF INVENTION

Technical Problem

In the ultrasonic diagnostic device described in Patent Literature 1, an ultrasonic output signal generated when a given bias voltage is applied to the CMUT cells or the like is measured, and the bias voltage is adjusted using the reciprocal of the ultrasonic output signal. However, in the CMUT cells, since the relationship of an input voltage-amplitude of an ultrasonic output signal is not linear, there is a problem in that an error is generated with this correction.

The present invention has been accomplished in consideration of the above-described problem, and an object of the invention is to provide an ultrasonic diagnostic device and an ultrasound probe capable of reducing variation in transmission and reception sensitivity among a plurality of CMUT cells even if a gap thickness, the thickness of a vibrating membrane, or the like varies.

Solution to Problem

In order to attain the above-described object, the invention provides an ultrasound probe including a plurality of CMUT cells each having an upper electrode and a lower electrode which are disposed opposite each other to apply a bias voltage, and a vibrating membrane which is disposed between the upper electrode and the lower electrode and vibrates during transmission and reception, and a transmission and reception sensitivity correction unit which corrects the bias voltage on the basis of correction data calculated using at least one parameter selected from the thickness of the vibrating membrane and the resonance frequency of the vibrating membrane.

Advantageous Effects of Invention

According to the invention, it is possible to provide an ultrasonic diagnostic device and an ultrasound probe capable of reducing variation in transmission and reception sensitivity among a plurality of CMUT cells even if a gap thickness, the thickness of a vibrating membrane, or the like varies.

BRIEF DESCRIPTION OF DRAWINGS

FIG. 2 is a configuration diagram showing an example of an ultrasonic diagnostic device according to the invention.

FIG. 4 is a configuration diagram showing another example of an ultrasonic diagnostic device according to the invention.

FIG. 7 is a comparison table of variation in transmission and reception sensitivity while changing a correction condition of a bias voltage.

FIG. 8 is a configuration diagram showing an ultrasonic diagnostic device according to another embodiment.

FIG. 12 is a configuration diagram showing another example of an ultrasonic diagnostic device according to the invention.

DESCRIPTION OF EMBODIMENTS

Figure 1:
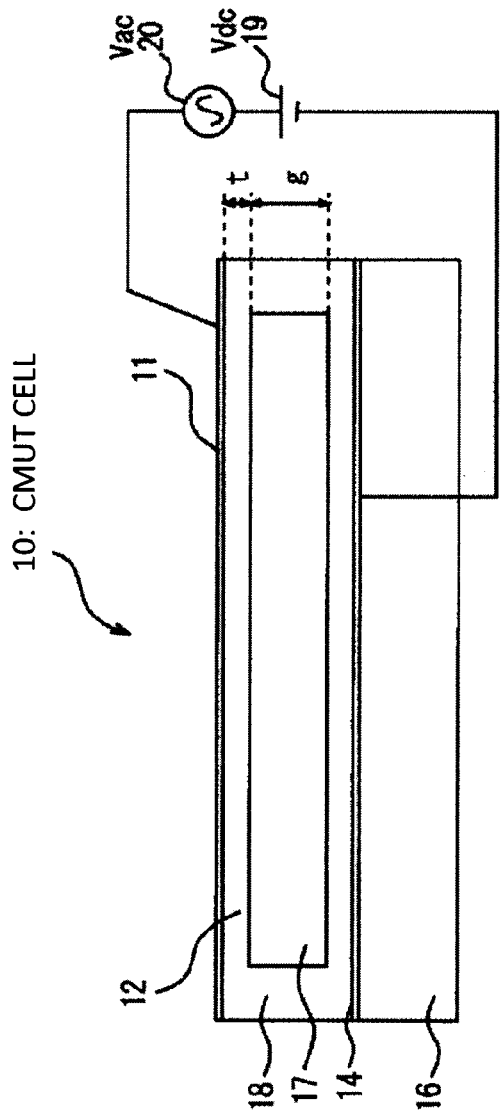
FIG. 1 is a schematic sectional view of a CMUT cell.

Embodiments of the invention will be described.

An ultrasonic diagnostic device of the invention includes an ultrasound probe which transmits an ultrasonic wave to an object and receives a reflected wave from the object, a transmission unit which transmits the ultrasonic wave, a reception unit which receives the reflected wave from the object, a control unit which controls the transmission unit and the reception unit, and a bias power source which supplies a bias voltage to the ultrasound probe, in which the ultrasound probe includes a plurality of CMUT cells each having an upper electrode and a lower electrode which are disposed opposite to each other to apply the bias voltage, and a vibrating membrane which is disposed between the upper electrode and the lower electrode and vibrates during transmission and reception, and a transmission and reception sensitivity correction unit which corrects the bias voltage supplied from the bias power source on the basis of correction data for correcting the bias voltage applied to the upper electrode and the lower electrode and supplies the corrected bias voltage to the upper electrode and the lower electrode, and the correction data is calculated using at least one parameter selected from the thickness of the vibrating membrane and the resonance frequency of the vibrating membrane.

The correction data is calculated using a value proportional to the absolute value of the difference between a reference frequency, which cancels the dimension of the resonance frequency, and the resonance frequency.

When the resonance frequency is f, the collapse voltage of each of the CMUT cells is $V_c$, and the value of $\beta$ as a real number is set within a range of $0<\beta<3$, the correction data is calculated using a value proportional to $V_c \cdot f^{-\beta}$ as the bias voltage applied to each of the CMUT cells.

The correction data is calculated using the thickness of the vibrating membrane of each of the CMUT cells and a collapse voltage of each of the CMUT cells.

The correction data is calculated using a value proportional to the absolute value of the difference between a reference thickness, which cancels the dimension of the thickness of the vibrating membrane of each of the CMUT cells, and the thickness.

When the thickness of the vibrating membrane of each of the CMUT cells is t, a collapse voltage of each of the CMUT cells is $V_c$, and the value of $\beta$ as a real number is set within a range of $0<\beta<3$, the correction data is calculated using a value proportional to $V_c \cdot t^{-\beta}$ as the bias voltage applied to each of the CMUT cells.

The transmission and reception sensitivity correction unit is provided for each CMUT cell.

The transmission and reception sensitivity correction unit is provided for every two or more CMUT cells.

The transmission and reception sensitivity correction unit is provided for each ultrasound probe.

An ultrasound probe of the invention includes a plurality of CMUT cells each having an upper electrode and a lower electrode which are disposed opposite to each other to apply a bias voltage, and a vibrating membrane which is disposed between the upper electrode and the lower electrode and vibrates during transmission and reception, and a transmission and reception sensitivity correction unit which corrects the bias voltage on the basis of correction data calculated using at least one parameter selected from the thickness of the vibrating membrane and the resonance frequency of the vibrating membrane.

The correction data is calculated using the resonance frequency and a collapse voltage of each of the CMUT cells.

When the resonance frequency is f, the collapse voltage of each of the CMUT cells is $V_c$, and the value of $\beta$ as a real number is set within a range of $0<\beta<3$, the correction data is calculated using a value proportional to $V_c \cdot f^{-\beta}$ as the bias voltage applied to each of the CMUT cells.

The correction data is calculated using the thickness of the vibrating membrane of each of the CMUT cells and a collapse voltage of each of the CMUT cells.

When the thickness of the vibrating membrane of each of the CMUT cells is t, a collapse voltage of each of the CMUT cells is $V_c$, and the value of $\beta$ as a real number is set within a range of $0<\beta<3$, the correction data is calculated using a value proportional to $V_c \cdot t^{-\beta}$ as the bias voltage applied to each of the CMUT cells.

Next, the details of an embodiment of the invention will be described by reference to the drawings. First, the configuration of a CMUT cell 10 will be described by reference to FIG. 1.

FIG. 1 is a schematic sectional view of the CMUT cell 10. The CMUT cell 10 has a configuration in which a vibrating membrane 12 provided with an upper electrode 11 and a substrate 16 provided with a lower electrode 14 are disposed opposite to each other, and the vibrating membrane 12 is supported by a support portion 18 such that a void 17 serving as a vacuum gap is formed between the vibrating membrane 12 and the substrate 16. In general, the upper electrode 11 is formed to be sufficiently thinner than the vibrating membrane 12 and to have a thickness such that hardness is negligible. A plurality of CMUT cells 10 shown in FIG. 1 are aggregated, thereby forming a CMUT chip. The structure of the CMUT cell 10 is not limited to that shown in FIG. 1, and, for example, other constituent elements may be added.

When an ultrasonic wave is transmitted from the CMUT cell 10, a DC bias voltage is applied between the upper electrode 11 and the lower electrode 14 by a bias power source 19 to generate an electrostatic attraction force, whereby the vibrating membrane 12 is deformed. An AC voltage is superimposed on the DC bias voltage by an AC power source 20, and the vibrating membrane 12 vibrates in an ultrasonic transmission and reception direction (an up-down direction of FIG. 1) to transmit an ultrasonic wave. When receiving an ultrasonic wave, since the vibrating membrane 12 is deformed with the reception of the ultrasonic wave, and the interval between the upper electrode 11 and the lower electrode 14 changes, change in electrostatic capacitance generated therefrom is detected by an AC component of an electrical signal.

FIG. 2 is a configuration diagram showing an example of an ultrasonic diagnostic device according to the invention. An ultrasonic diagnostic device 30 shown in FIG. 2 includes an ultrasound probe 31 and an ultrasonic diagnostic device body 32.

The ultrasound probe 31 includes CMUT cells 10-1 to 10-n in which transmission and reception sensitivity changes depending on the bias voltage to be applied. The ultrasound probe 31 further includes a storage unit 34 which stores data (hereinafter, referred to as correction data) for correcting a bias voltage of each of the CMUT cells 10-1 to 10-n, and transmission and reception sensitivity correction units 35-1 to 35-n which correct the bias voltage to be applied to each of the CMUT cells 10-1 to 10-n to a value according to the correction data to thereby correct variation in transmission and reception sensitivity of the CMUT cells 10-1 to 10-n. The storage unit 34 stores correction data, in the form of the value of the bias voltage to be applied to each of the CMUT cells 10-1 to 10-*n*, as digital data, and has, for example, a ROM, a flash memory, or the like. The correction data may be stored in a binary code of 0 and 1 by means of a switch, a jumper pin, or the like.

The ultrasonic diagnostic device body 32 has a bias power source (DC power source) 37 which supplies a bias voltage, a transmission unit 38 which causes the ultrasound probe 31 to output a transmission signal to an object, a reception unit 39 which converts a reflected wave reflected from the object to a reception signal using the ultrasound probe 31, and amplifies and phases the reception signal, an image processing unit 42 which generates an image signal using the reception signal, a display unit 48 which displays the generated image signal, a transmission and reception separation unit 40 which separates the transmission signal and the reception signal, a control unit 36 which controls the transmission unit 38, the reception unit 39, and the image processing unit 42, and an input unit 47 which inputs control parameters of respective elements to be controlled by the control unit 36. The control unit 36 includes a correction control unit 36*a* which reads the correction data from the storage unit 34 and transmits the correction data to the transmission and reception sensitivity correction units 35-1 to 35-*n*. The correction data read from the storage unit 34 by the control unit 36 is transmitted to the transmission and reception sensitivity correction units 35-1 to 35-*n*.

In the example of FIG. 2, one transmission and reception sensitivity correction unit is provided for each CMUT cell, and different corrected bias voltages are applied to the respective CMUT cells. With this, since different corrected bias voltages are applied to the respective CMUT cells and accurate bias voltages can be individually applied to the CMUT cells, it is possible to accurately correct variation in transmission and reception sensitivity of each of the CMUT cells. Although one transmission and reception sensitivity correction unit is provided for one CMUT cell, and different corrected bias voltages are applied to the respective CMUT cells, one transmission and reception sensitivity correction unit may be provided for two or more CMUT cells, and the same corrected bias voltage may be applied to two or more CMUT cells.

With this, since a bias power source which applies the bias voltage to be applied to each of the CMUT cells having substantially the same variation in transmission and reception sensitivity, wiring or the like can be shared, thus contributing to reduction in circuit scale.

A circuit in which one transmission and reception sensitivity correction unit is provided for one CMUT cell and different corrected bias voltages are applied to the CMUT cells and a circuit in which one transmission and reception sensitivity correction unit is provided for two or more CMUT cells and the same corrected bias voltage is applied to two or more CMUT cells may be mixed. With this, it is possible to use the advantages of both accurate correction of variation in transmission and reception sensitivity in the CMUT cells and reduction in circuit scale realized by sharing.

Figure 3:
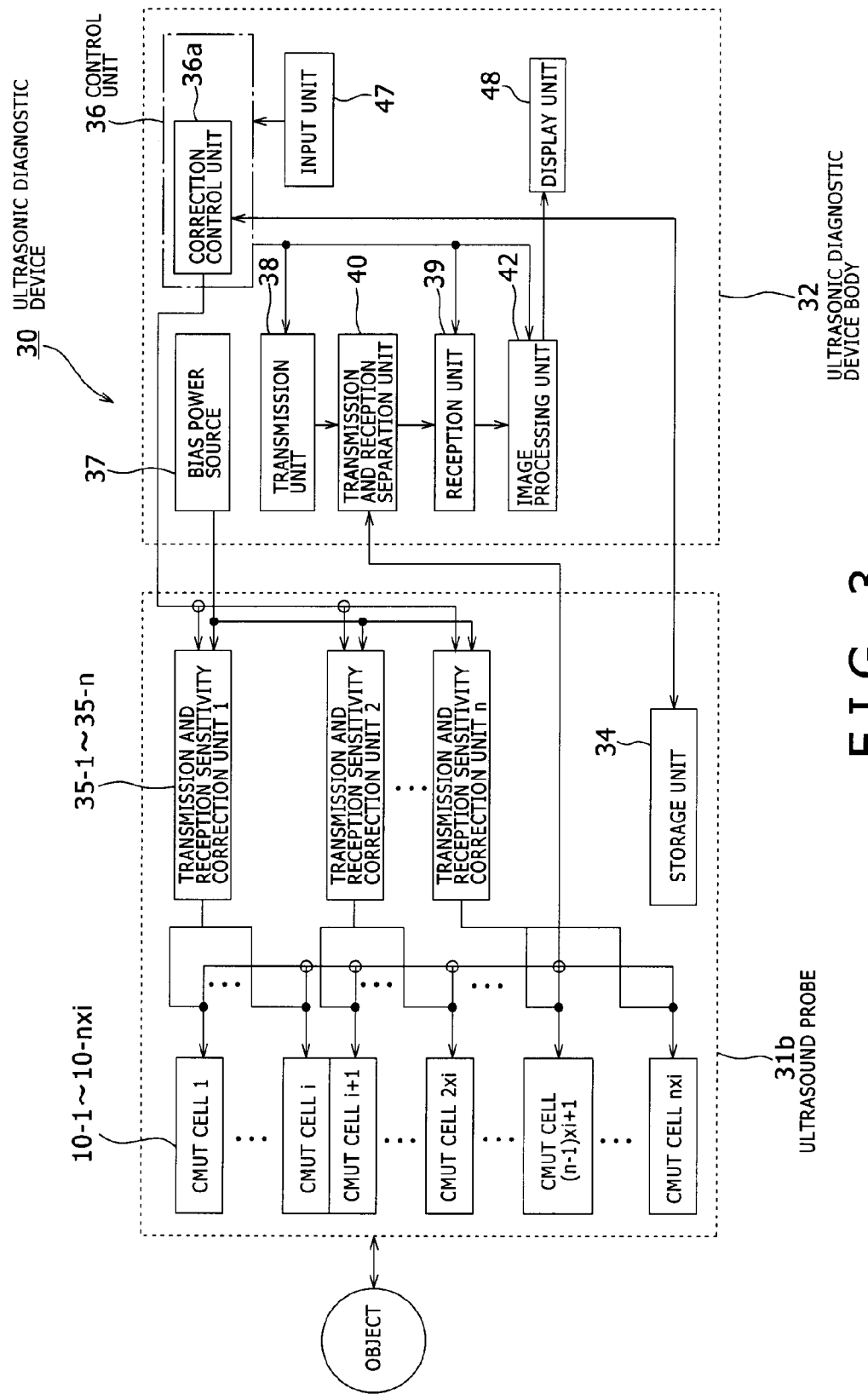
FIG. 3 is a configuration diagram showing another example of an ultrasonic diagnostic device according to the invention.

FIG. 3 is a configuration diagram showing another example of an ultrasonic diagnostic device according to the invention. In an ultrasound probe 31*b* of an ultrasonic diagnostic device 30 shown in FIG. 3, as described above, one transmission and reception sensitivity correction unit is provided for i (where i≥2) CMUT cells, CMUT cells 10-1 to 10-*i* are connected to a transmission and reception sensitivity correction unit 35-1, CMUT cells 10-*i*+1 to 10-2×i are connected to a transmission and reception sensitivity correction unit 35-2, and subsequently, similar connection is made. Note that it may be the case that only one transmission and reception sensitivity correction unit is provided in one ultrasound probe.

The transmission and reception sensitivity correction units are not necessarily provided in the ultrasound probe, and may be provided in, for example, the ultrasonic diagnostic device body. The storage unit 34 is not necessarily provided in the ultrasound probe, and may be provided in, for example, an external device, such as a personal computer including a hard disk drive.

FIG. 12 is a configuration diagram showing another example of an ultrasonic diagnostic device according to the invention. In an ultrasonic diagnostic device 30 shown in FIG. 12, transmission and reception sensitivity correction units 35-1 to 35-*n* are provided in an ultrasonic diagnostic device body 32, instead of an ultrasound probe 31. With this configuration of the ultrasonic diagnostic device 30, since it is possible to reduce the number of wirings from the ultrasonic diagnostic device body 32 to the ultrasound probe 31, it becomes possible to realize reduction in cost of the entire device or reduction in weight of an ultrasound probe cable. The transmission and reception sensitivity correction units 35-1 to 35-*n* are disposed in the ultrasonic diagnostic device body 32, whereby it is not necessary to provide the transmission and reception sensitivity correction units 35-1 to 35-*n* in the ultrasound probe 31, making it possible to achieve compactness of the ultrasound probe 31 and reduction in cost.

FIG. 4 is a configuration diagram showing another example of an ultrasonic diagnostic device according to the invention. An ultrasonic diagnostic device 30 shown in FIG. 4 includes an external device 41 having a personal computer or the like, and a storage unit 34 having a hard disk drive or the like is provided in the external device 41. The external device 41 is provided with a correction control unit 36*a*, and an ultrasonic diagnostic device body 32 is provided with a control unit 36*b*. The correction control unit 36*a* reads correction data from the storage unit 34 and transmits the correction data to the control unit 36*b* through a communication unit having a LAN (Local Area Network) or the like, and the control unit 36*b* transmits the correction data to transmission and reception sensitivity correction units 35-1 to 35-*n*.

For the external device 41 shown in FIG. 4, for example, a remote server or the like may be used. At this time, it is desirable that correction data associated with the identification number of the ultrasound probe 31 is stored in the remote server in advance. The correction data stored in the storage unit 34 may be recorded in a CD (Compact Disk), a Floppy (Registered Trademark) disk, or the like, may be distributed along with the ultrasound probe 31, and may be stored in the storage unit 34. Note that other constituent elements are the same as those of the ultrasonic diagnostic device 30 shown in FIG. 2, and thus description thereof will not be repeated.

Figure 5:
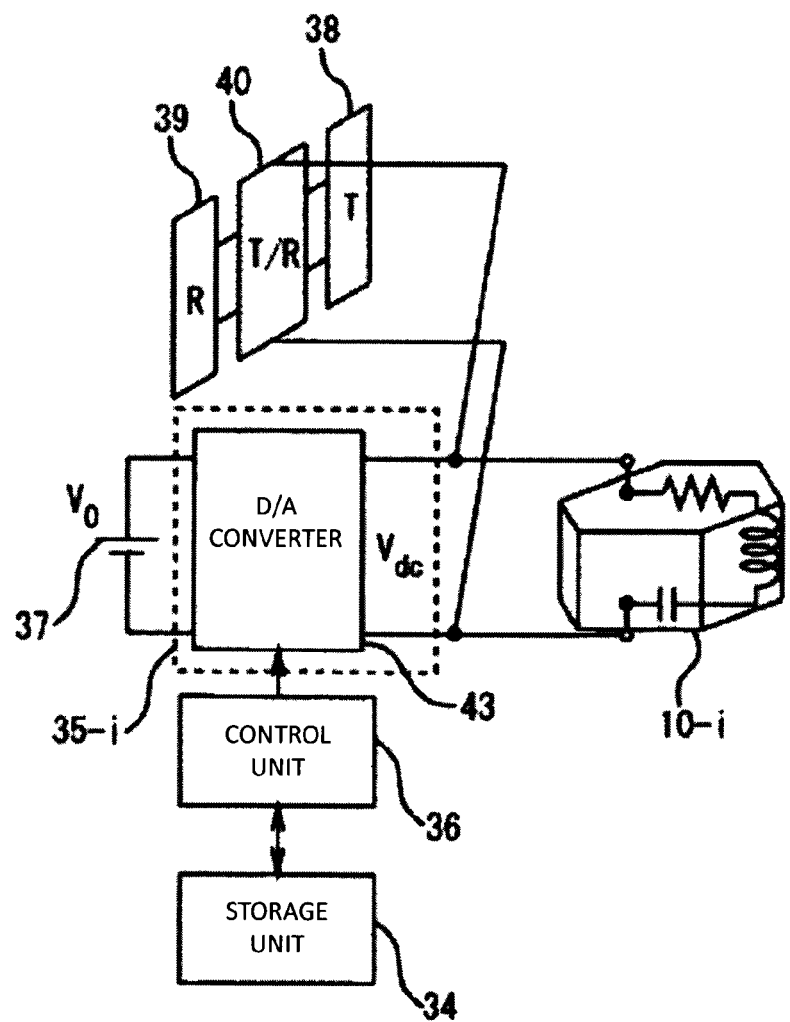
FIG. 5 is a diagram showing an example of a specific configuration of one transmission and reception sensitivity correction unit.

Next, the specific configuration of the transmission and reception sensitivity correction units 35-1 to 35-*n* will be described. FIG. 5 is a diagram showing an example of a specific configuration of one transmission and reception sensitivity correction unit 35-*i*. In the example of FIG. 5, a D/A converter 43 serving as the transmission and reception sensitivity correction unit 35-*i* is disposed between a CMUT cell 10-*i* and a bias power source 37, and the correction data read from the storage unit 34 is transmitted to the D/A converter 43 by the control unit 36, thereby controlling a bias voltage to be applied to the CMUT cell 10-*i*. Normally, since a resistance circuit is embedded in the D/A converter 43, there is configured a mechanism in which an internal resistor is switched by the correction data transmitted from the control unit 36 to control the bias voltage.

The transmission and reception sensitivity correction units 35-1 to 35-n are not limited to the example of FIG. 5 insofar as these have a function of correcting the bias voltage by the control unit 36. For example, an electronic switch or the like may be controlled by the control unit 36 to switch the resistance circuit. In the example of FIG. 5, although one transmission and reception sensitivity correction unit 35-i is provided for one CMUT cell 10-i, one transmission and reception sensitivity correction unit may be provided for two or more CMUT cells, and the same bias voltage may be applied to a plurality of CMUT cells.

Next, a method of correcting transmission and reception sensitivity of the CMUT cell 10 which is performed in the ultrasonic diagnostic device of the invention will be described by reference to a numerical expression. In the invention, the bias voltage is corrected on the basis of a parameter responsible for variation in transmission and reception sensitivity of the CMUT cell 10 or an alternative parameter, whereby the transmission and reception sensitivity of the CMUT cell 10 is corrected and variation in transmission and reception sensitivity among a plurality of CMUT cells is reduced. The correction of the bias voltage is performed by the above-described transmission and reception sensitivity correction units 35-1 to 35-n or the like.

The transmission or reception sensitivity of the CMUT cell 10 is provided by a voltage-force conversion coefficient. Hereinafter, a parameter of the CMUT cell 10 which determines the conversion coefficient will be described. As shown in FIG. 1, the CMUT cell 10 has a so-called capacitor structure in which two sheets of electrodes are disposed opposite to each other, and electrostatic energy W is provided by Expression (1) when electrostatic capacitance is C and a voltage is V.

$$W = \frac{1}{2} C \cdot V^2 \quad (1)$$

The energy W of Expression (1) is the product of a force F applied to the vibrating membrane 12 and a gap thickness g shown in FIG. 1, and since the electrostatic capacitance C is $C = \varepsilon_0 \cdot S/g$ when $\varepsilon_0$ is a vacuum dielectric constant and S is the area of the vibrating membrane 12, the force F which is generated by the electrostatic energy is provided by Expression (2).

$$W = F \cdot g = \frac{1}{2} \left( \frac{\varepsilon_0 S}{g} \right) \cdot V^2 \quad (2)$$

$$F = \frac{1}{2} \left( \frac{\varepsilon_0 S}{g} \right) \cdot \frac{V^2}{g}$$

Since the voltage V of Expression (2) is the sum of a bias voltage $V_{dc}$ of a transmission signal or a reception signal and an AC voltage $V_{ac}$, $V = V_{dc} + V_{ac}$ is substituted into Expression (2), thereby obtaining Expression (3).

$$F = \frac{1}{2} \left( \frac{\varepsilon_0 S}{g} \right) \cdot \frac{(V_{dc} + V_{ac})^2}{g} \quad (3)$$

$$= \frac{1}{2} \cdot \left( \frac{\varepsilon_0 S}{g} \right) \cdot \frac{1}{g} (V_{dc}^2 + 2 V_{dc} V_{ac} + V_{ac}^2)$$

When obtaining the transmission and reception sensitivity of the CMUT cell 10 from Expression (3), since the transmission and reception sensitivity is the conversion coefficient of the AC voltage $V_{ac}$ as a signal and the force, the component of a force only resulting from the bias voltage $V_{dc}$ of the first term of Expression (3) is not necessarily considered and is negligible. If it is assumed that $V_{ac}$ is sufficiently smaller than $V_{dc}$, since the third term of Expression (3) is extremely smaller than other terms and thus negligible, Expression (3) may be abbreviated as (4).

$$F = \frac{1}{2} \left( \frac{\varepsilon_0 S}{g} \right) \cdot \frac{2 V_{dc} V_{ac}}{g} \quad (4)$$

$$= \left( \frac{\varepsilon_0 S}{g} \right) \cdot \frac{V_{dc} V_{ac}}{g}$$

From Expression (4), a voltage-force conversion coefficient Nu is provided by Expression (5).

$$Nu = F / V_{ac} \quad (5)$$

$$= \frac{\varepsilon_0 S}{g} \cdot \frac{V_{dc}}{g}$$

$$\propto C \cdot E$$

$$\propto \frac{V_{dc}}{g^2}$$

In Expression (5), E is an electric field when the bias voltage is applied, and $E = V_{dc}/g$. In Expression (5), $\propto$ represents a proportional relationship, and hereinafter, is similarly used. As shown in Expression (5), the voltage-force conversion coefficient Nu of the CMUT cell 10 is inversely proportional to the second power of the gap thickness g and is proportional to the bias voltage $V_{dc}$. Accordingly, it is understood that variation in transmission and reception sensitivity of the CMUT cell 10 is significantly influenced by variation in the gap thickness g.

In the transmission and reception sensitivity of the CMUT cell 10; that is, the voltage-force conversion coefficient Nu, in order to reduce the influence of the gap thickness g, in general, a method which uses a collapse voltage as a bias voltage is used. The collapse voltage is a bias voltage generated when the vibrating membrane 12 comes into contact with an opposite surface. A theoretical relational expression of the collapse voltage $V_c$ can be expressed by Expression (6) when k is a spring constant of the vibrating membrane 12.

$$V_c = \sqrt{\frac{8 k g^3}{27 \varepsilon_0 S}} \quad (6)$$

Since the vibrating membrane 12 of the CMUT cell 10 has a plate spring structure, the spring constant k of Expression (6) is proportional to the third power of the thickness t of the vibrating membrane 12 shown in FIG. 1 ($k \propto t^3$). Accordingly, the collapse voltage $V_c$ is expressed by Expression (7).

$$V_c \propto t^{\frac{3}{2}} \cdot g^{\frac{3}{2}} \quad (7)$$

From Expression (5) and Expression (7), as shown in Expression (8), the transmission and reception sensitivity Nu of the CMUT cell 10 when the bias voltage $V_{dc}$ is set to a value proportional to the collapse voltage $V_c$ ($V_{dc} \propto V_c$) can be obtained as an expression proportional to the power of the gap thickness g and the thickness t of the vibrating membrane 12.

$$Nu \propto \frac{V_c}{g^2} \quad (8)$$
$$\propto \frac{t^{\frac{3}{2}} \cdot g^{\frac{3}{2}}}{g^2}$$
$$\propto t^{\frac{3}{2}} \cdot g^{-\frac{1}{2}}$$

Accordingly, the collapse voltage $V_c$ is used, whereby the influence of the gap thickness g on the transmission and reception sensitivity of the CMUT cell 10 can be significantly reduced from the second power to the ½ power (Expression (8) and Expression (5)). However, secondarily, the influence of the thickness t of the vibrating membrane 12 comparatively significantly increases due to the use of the collapse voltage $V_c$.

In order to solve this problem, the invention describes a method in which the bias voltage is corrected on the basis of a parameter proportional to the resonance frequency of the vibrating membrane 12 of the CMUT cell 10 in the ultrasonic transmission and reception direction as a parameter proportional to the thickness t of the vibrating membrane 12, thereby reducing variation in transmission and reception sensitivity of the CMUT cell 10.

The resonance frequency of the vibrating membrane 12 of the CMUT cell 10 in the ultrasonic transmission and reception direction is a frequency at which the vibrating membrane 12 vibrates in a highest energy efficiency state. In general, a resonance frequency f of a spring material of the vibrating membrane 12 of the CMUT cell 10 can be expressed by Expression (9) when the spring constant of the vibrating membrane 12 is k and the mass of the vibrating membrane 12 is m.

$$f = \frac{1}{2\pi} \sqrt{\frac{k}{m}} \quad (9)$$

In Expression (9), the mass m of the vibrating membrane 12 is the product of density and volume, and since the volume is proportional to the thickness t of the vibrating membrane 12, the mass m is proportional to the thickness t of the vibrating membrane 12 ($m \propto t$). If the spring constant k is proportional to the third power of the thickness t of the vibrating membrane 12 ($k \propto t^3$) is considered, Expression (9) can be abbreviated as Expression (10).

$$f \propto \sqrt{\frac{t^3}{t}} \quad (10)$$
$$\propto t$$

From Expression (10), it is understood that the resonance frequency f is proportional to the thickness t of the vibrating membrane 12. For this reason, the resonance frequency f can be regarded as a parameter which provides the thickness t of the vibrating membrane 12. The resonance frequency f of the vibrating membrane 12 of the CMUT cell 10 in the ultrasonic transmission and reception direction can be measured using an impedance meter or the like. From the above-described expressions, it is understood that the bias voltage to be applied to each CMUT cell 10 is corrected using the collapse voltage $V_c$ of the CMUT cell 10 and the resonance frequency f of the vibrating membrane 12 in the ultrasonic transmission and reception direction or the thickness t of the vibrating membrane 12, thereby reducing the influence of manufacturing variation of the CMUT chip.

In the invention, as a parameter proportional to the resonance frequency of the vibrating membrane 12 of the CMUT cell 10 in the ultrasonic transmission and reception direction, there is used the resonance frequency f of the vibrating membrane 12 of the CMUT cell 10 in the ultrasonic transmission and reception direction, the measured value of the thickness t of the vibrating membrane 12 of the CMUT cell 10, or the estimated value of the thickness t of the vibrating membrane 12 of the CMUT cell 10.

The thickness t of the vibrating membrane 12 of the CMUT cell 10 may be measured using any method. However, since the vibrating membrane 12 cannot be structurally observed by a microscope or the like or the CMUT cell 10 is minute and accordingly a measurement method is limited, it may be the case that non-destructive measurement is not easily performed, and it is difficult to directly obtain the measured value of the thickness t of the vibrating membrane 12.

Accordingly, there is known a method which uses the estimated value of the thickness t of the vibrating membrane 12, instead of the measured value of the thickness t of the vibrating membrane 12. The method which uses the estimated value of the thickness t of the vibrating membrane 12 is a method in which the CMUT cell 10 of a CMUT chip (hereinafter, referred to as a dummy chip) which is not used as a transducer is destroyed and the thickness t of the vibrating membrane 12 is measured to estimate the thickness t of the vibrating membrane 12 of the CMUT cell 10 of a CMUT chip (hereinafter, referred to as a target chip) which is used as a transducer.

This method assumes that variation in the thickness t of the vibrating membrane 12 is dominantly influenced by manufacturing variation during heat treatment or the like. Since a CMUT chip is formed on a semiconductor wafer (hereinafter, referred to as a wafer) as an IC chip or the like, variation in the thickness t of the vibrating membrane 12 is present for each wafer lot, and has a distribution on the same wafer. Accordingly, it is considered that the distribution of the thickness t of the CMUT cell 10 of the CMUT chip on the same wafer or an adjacent CMUT chip is examined, thereby estimating the distribution of the thickness t of the vibrating membrane of the target chip.

Next, as in Expression (11), there will be described a method in which the bias voltage is corrected using a parameter proportional to the resonance frequency of the vibrating membrane 12 of the CMUT cell 10 in the ultrasonic transmission and reception direction and the collapse voltage of the CMUT cell 10. Hereinafter, the bias voltage corrected by the method of the invention is referred to as a corrected bias voltage.

$$V_{dc} = \alpha \cdot V_c \cdot \left(\frac{f}{f_0}\right)^{-\frac{3}{2}} \tag{11}$$

In Expression (11), $\alpha$ is a real number constant for setting such that the corrected bias voltage $V_{dc}$ does not exceed the collapse voltage $V_c$ which is an allowable voltage value of the CMUT cell 10 for use, and is set to, for example, a value from 0 to 1. Here, it is assumed that f is the resonance frequency of the vibrating membrane 12 of the CMUT cell 10 in the ultrasonic transmission and reception direction. $f_0$ is a reference frequency which cancels the dimension of the resonance frequency f from the function of the corrected bias voltage $V_{dc}$. As for $f_0$, for example, a center frequency at the time of design of the resonance frequency of the vibrating membrane 12 may be given, or the average value, the median value, or the like of the measured values of the resonance frequency may be used.

If Expression (7) is substituted into Expression (11) and Expression (10) is further used, as in Expression (12), it is possible to cancel the influence of the thickness t of the vibrating membrane 12.

$$V_{dc} \propto \alpha \cdot t^{\frac{3}{2}} \cdot g^{\frac{3}{2}} \left(\frac{f}{f_0}\right)^{-\frac{3}{2}} \tag{12}$$

$$\propto \alpha \cdot g^{\frac{3}{2}} \cdot f_0^{\frac{3}{2}}$$

From Expression (5) and Expression (12), a transmission and reception sensitivity Nu' for a corrected bias voltage can be expressed by Expression (13).

$$Nu' \propto \frac{V_{dc}}{g^2} \tag{13}$$

$$Nu' \propto \frac{\alpha \cdot g^{\frac{3}{2}} \cdot f_0^{\frac{3}{2}}}{g^2}$$

$$\propto \alpha \cdot g^{-\frac{1}{2}}$$

Accordingly, with the use of the corrected bias voltage of Expression (11), it is possible to remove the influence of variation in the thickness t of the vibrating membrane 12.

In Expression (11), although the resonance frequency f is used as the parameter proportional to the resonance frequency, and the resonance frequency f and the reference frequency $f_0$ are used, the resonance frequency f and the reference frequency $f_0$ can be respectively replaced with the measured value of the thickness t of the vibrating membrane 12 of the CMUT cell 10 and the reference thickness $t_0$ of the vibrating membrane 12. When the thickness t of the vibrating membrane 12 cannot be directly measured, the resonance frequency f and the reference frequency $f_0$ can be respectively replaced with the estimated value of the thickness t of the vibrating membrane 12 of the CMUT cell 10 and the reference thickness $t_0$ of the vibrating membrane 12.

This is because, as shown in Expression (10), the resonance frequency f is proportional to the thickness t of the vibrating membrane 12.

When performing bias correction shown in Expression (11), a corrected bias voltage may be easily determined by a function of an approximate expression using the resonance frequency f or the thickness t of the vibrating membrane 12. For example, when the difference between the resonance frequency f and the reference frequency $f_0$ is sufficiently small, a corrected bias voltage may be approximately determined by the same approach as the above-described correction method. If the difference between the resonance frequency f and the reference frequency $f_0$ is $\Delta f$ ($=f-f_0$), Expression (11) can be expressed by Expression (14).

$$V_{dc}(\Delta f) = \alpha \cdot V_c \cdot \left(\frac{f}{f_0}\right)^{-\frac{3}{2}} \tag{14}$$

$$= \alpha \cdot V_c \cdot \left(\frac{f_0 + \Delta f}{f_0}\right)^{-\frac{3}{2}}$$

$$= \alpha \cdot V_c \cdot \left(1 + \frac{\Delta f}{f_0}\right)^{-\frac{3}{2}}$$

Expression (14) is expressed by Expression (15) through Taylor series Development.

$$V_{dc} = \sum_{n=1}^{m} \frac{V_{dc}^{(n)}(0)}{n!} \cdot \Delta f^n \tag{15}$$

In Expression (15), $V_{dc}^{(n)}(\Delta f)$ is an n-th order differentiation of $V_{dc}$ by $\Delta f$.

In Expression (15), m can have an arbitrary value. For example, if first order approximation is taken as m=1, Expression (16) is obtained.

$$V_{dc} \cong \alpha \cdot V_c \cdot \left(1 - \frac{3}{2}\frac{\Delta f}{f_0}\right) \tag{16}$$

The invention is not limited to Taylor series development, and may be applied to the approximation or superposition of Expressions (14) to (16).

As shown in Expressions (17) and (18), Expressions (11) and (16) can have a width in a settable corrected bias voltage when a real number index is $\beta$.

$$\alpha V_c \left(\frac{f}{f_0}\right)^{-\beta} \leq V_{dc} < V_c \tag{17}$$

$$\left(\alpha < \left(\frac{f}{f_0}\right)^{\beta}\right)$$

In Expression (17), it is desirable that the following expression is established.

$$V_{dc} = \alpha \cdot V_c \cdot \left(\frac{f}{f_0}\right)^{-\frac{3}{2}} \tag{17a}$$

-continued $$\alpha V_c \left(1 - \beta \frac{\Delta f}{f_0}\right) \leq V_{dc} < V_c \quad (18)$$

$$\left(\alpha < \left(1 - \beta \frac{\Delta f}{f_0}\right)^{-1}\right)$$

In Expression (18), it is desirable that the following expression is established.

$$V_{dc} = \alpha \cdot V_c \cdot \left(1 - \frac{3}{2} \frac{\Delta f}{f_0}\right) \quad (18a)$$

When the corrected bias voltage of Expression (17) is used, the transmission and reception sensitivity Nu" for a corrected bias voltage is expressed by Expression (19).

$$Nu'' \propto t^{\left(\frac{3}{2} - \beta\right)} \cdot g^{-\frac{1}{2}} \quad (19)$$

In Expression (19), when β=3/2=1.5, the influence of the thickness t of the vibrating membrane 12 on the transmission and reception sensitivity is minimized.

Here, the range of β such that variation in transmission and reception sensitivity Nu" when the corrected bias voltage of Expression (17) is used is smaller than variation in transmission and reception sensitivity Nu when bias correction is performed only using the collapse voltage by Expression (8), and Expression (19) is determined.

As a measure of variation in transmission and reception sensitivity, for example, when an average value in a wafer lot or a statistical value, such as variation, is used, relative errors are used. Since variations in the gap thickness g and the thickness t of the vibrating membrane 12 are separated from each other, it is assumed that there is no correlation; that is, covariance is 0. Relative errors when bias correction is performed only using the collapse voltage and when the corrected bias voltage of Expression (17) is used are respectively expressed by Expressions (20) and (21) when the variations of the vibrating membrane thickness t and the gap thickness g are respectively $\sigma_t^2$ and $\sigma_g^2$.

$$\left(\frac{\sigma_{Nu}}{Nu}\right)^2 = \left(\frac{1}{Nu} \frac{\partial Nu}{\partial g}\right)^2 \cdot \sigma_g^2 + \left(\frac{1}{Nu} \frac{\partial Nu}{\partial t}\right)^2 \cdot \sigma_t^2 \quad (20)$$

$$\left(\frac{\sigma_{Nu''}}{Nu''}\right)^2 = \left(\frac{1}{Nu''} \frac{\partial Nu''}{\partial g}\right)^2 \cdot \sigma_g^2 + \left(\frac{1}{Nu''} \frac{\partial Nu''}{\partial t}\right)^2 \cdot \sigma_t^2 \quad (21)$$

In Expressions (20) and (21), $\sigma_{Nu}^2$ and $\sigma_{Nu''}^2$ are the variances of transmission and reception sensitivity.

In order to make variation in transmission and reception sensitivity Nu" when the corrected bias voltage of Expression (17) is used be smaller than variation in transmission and reception sensitivity Nu when bias correction is performed only using the collapse voltage, it should suffice that the relative error satisfies Expression (22).

$$\left(\frac{\sigma_{Nu}}{Nu}\right)^2 > \left(\frac{\sigma_{Nu''}}{Nu''}\right)^2 \quad (22)$$

If Expressions (8) and (19) are substituted into Expressions (20) and (21) and partial differentiation is performed, Expressions (23) and (24) are obtained.

$$\left(\frac{\sigma_{Nu}}{Nu}\right)^2 = \left(\frac{1}{2} \frac{\sigma_g}{g}\right)^2 + \left(\frac{3}{2} \frac{\sigma_t}{t}\right)^2 \quad (23)$$

$$\left(\frac{\sigma_{Nu''}}{Nu''}\right)^2 = \left(\frac{1}{2} \frac{\sigma_g}{g}\right)^2 + \left(\left(\frac{3}{2} - \beta\right) \frac{\sigma_t}{t}\right)^2 \quad (24)$$

Then, Expressions (23) and (24) are substituted into Expression (22), whereby Expression (25) is obtained. (25)

$$\left(\frac{1}{2} \frac{\sigma_g}{g}\right)^2 + \left(\frac{3}{2} \frac{\sigma_t}{t}\right)^2 > \left(\frac{1}{2} \frac{\sigma_g}{g}\right)^2 + \left[\left(\frac{3}{2} - \beta\right) \frac{\sigma_t}{t}\right]^2 \quad (25)$$

$$\left(\frac{3}{2}\right)^2 > \left(\frac{3}{2} - \beta\right)^2$$

$$0 > \beta(\beta - 3)$$

$$0 < \beta < 3$$

Accordingly, the range of β such that variation in transmission and reception sensitivity Nu" when the corrected bias voltage of Expression (17) is used is smaller than variation in transmission and reception sensitivity Nu when bias correction is performed only using the collapse voltage becomes as shown in Expression (25).

In this way, the value of β is set within a range of 0<β<3, and the bias voltage is corrected as shown in Expression (17), thereby determining the corrected bias voltage.

Expression (11) may be generalized as Expression (26), thereby determining the value of the corrected bias voltage $V_{dc}$.

$$V_{dc} = \alpha \cdot V_c \cdot \left(\frac{f}{f_0}\right)^{-\beta} \quad (26)$$

At this time, as in Expression (17), the value of α may be set to $\alpha < (f/f_0)^\beta$, and as in Expression (25), the value of β may be set within a range of 0<β<3. In Expression (26), α is a constant for setting such that the corrected bias voltage $V_{dc}$ does not exceed the collapse voltage $V_c$ which is an allowable voltage value of the CMUT cell 10 for use. The corrected bias voltage $V_{dc}$ is set to a value proportional to the collapse voltage $V_c$, whereby, as shown in Expression (8), it is possible to reduce the influence of the gap thickness g on the transmission and reception sensitivity of the CMUT cell 10. Furthermore, the corrected bias voltage $V_{dc}$ is set to a value proportional to $(f/f_0)^{-\beta}$, whereby, as shown in Expressions (12) and (19), it is possible to reduce the influence of the thickness t of the vibrating membrane 12 on the transmission and reception sensitivity of the CMUT cell 10.

Since Expression (26) is proportional to $V_c \cdot f^{-\beta}$, the bias voltage to be applied to the CMUT cell 10 may be corrected to a value proportional to $V_c \cdot f^{-\beta}$. At this time, as in Expression (25), the value of β may be set within a range of 0<β<3.

Expression (16) may be generalized as Expression (27), and the bias voltage to be applied to the CMUT cell 10 may be corrected to a value proportional to $V_c \cdot (1 - \beta \cdot |f - f_0|/f_0)$.

$$V_{dc} \propto V_c \cdot \left(1 - \beta \frac{|\Delta f|}{f_0}\right) \quad (27)$$

At this time, as in Expression (25), the value of β may be set within a range of 0<β<3.

In the numerical expressions, although description will be provided using the resonance frequency f and the reference frequency $f_0$, these may be respectively replaced with the measured value of the thickness t of the vibrating membrane 12 of the CMUT cell 10 and the reference thickness t of the vibrating membrane 12. The resonance frequency f and the reference frequency $f_0$ may be respectively replaced with the estimated value of the thickness t of the vibrating membrane 12 of the CMUT cell 10 and the reference thickness t of the vibrating membrane 12.

The reference thickness $t_0$ of the vibrating membrane 12 is a constant, and a design value may be provided or the average value or the like of the measured values or the estimated values of the thickness t of the vibrating membrane 12 may be provided.

Figure 6:
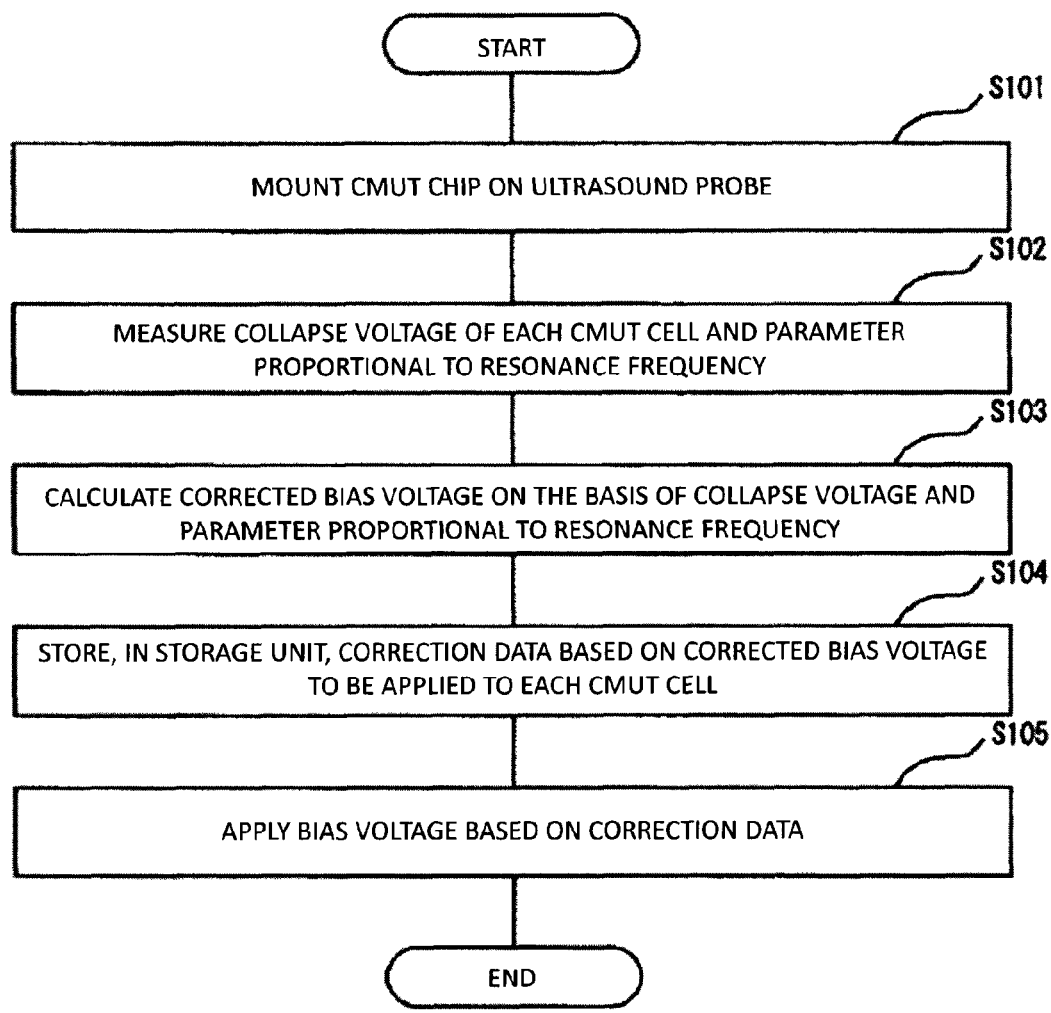
FIG. 6 is a flowchart showing a procedure of transmission and reception sensitivity correction according to the invention.

Next, a procedure of transmission and reception sensitivity correction of the CMUT cell 10 according to the invention will be described. FIG. 6 is a flowchart showing a procedure of transmission and reception sensitivity correction according to the invention.

First, a CMUT chip is mounted on the ultrasound probe 31 (S101).

Then, the collapse voltage of each CMUT cell 10 and the parameter proportional to the resonance frequency of the vibrating membrane 12 in the ultrasonic transmission and reception direction are measured (S102).

First, a method of measuring the collapse voltage of the CMUT cell 10 in S102 will be described. The collapse voltage is a voltage generated when the vibrating membrane 12 comes into contact with the opposite surface; that is, the gap thickness g is minimized. Since the gap thickness g is inversely proportional to the electrostatic capacitance, the collapse voltage can be measured with the electrostatic capacitance as an index. During measurement, the bias voltage may gradually increase to the CMUT cell 10 to measure the electrostatic capacitance, and an application voltage when the electrostatic capacitance value has a maximum value may be determined.

Next, a method of measuring the resonance frequency of the vibrating membrane 12 in the ultrasonic transmission and reception direction in S102 will be described. Since a vibration model of the vibrating membrane 12 of the CMUT cell 10 in the ultrasonic transmission and reception direction can be expressed by a serial model of a resistor, a capacitor, and a coil as an equivalent circuit, the frequency at which the joint impedance of the resistor, the capacitor, and the coil is minimized becomes the resonance frequency.

In the invention, when measuring the resonance frequency, electrical impedance between the upper electrode 11 and the lower electrode 14 is measured by an impedance meter. For means for measuring the resonance frequency, in addition to the impedance meter, comparable means may be used. For example, a current value when a given voltage is applied to a measurement target including the CMUT cell 10 may be measured, and impedance may be determined as a quotient of a voltage and a current to determine the resonance frequency. Alternatively, the CMUT cell 10 to be measured may be embedded in a bridge circuit, and a balance may be determined to perform measurement. At this time, the frequency changes near a frequency as a reference, such as the design value of the resonance frequency, making it possible to perform measurement in a shorter time.

As shown in FIG. 3, when the same bias voltage is applied to two or more CMUT cells 10, the collapse voltage and the resonance frequency are measured in a state where a plurality of CMUT cells to which the same bias voltage is applied are connected in parallel. Alternatively, a representative value, an average value, or the like may be determined from the collapse voltage of each CMUT cell 10 and the resonance frequency and used.

As described above, as the parameter proportional to the resonance frequency, the measured value or estimated value of the thickness t of the vibrating membrane 12 may be determined, instead of the resonance frequency. When determining the estimated value of the thickness t of the vibrating membrane 12, it should suffice that a CMUT chip which is not used as a transducer near a CMUT chip as a transducer or on the same wafer is set as a dummy chip, the CMUT cell 10 in the dummy chip is destroyed, and the thickness t of the vibrating membrane 12 is measured from a section to determine the estimated value.

For example, when reducing variation in transmission and reception sensitivity for every plurality of CMUT cells 10, a chip adjacent to a target chip on a wafer; desirably, chips on both sides of the target chip, are set as dummy chips, and there is measured the thickness t of the vibrating membrane 12 of at least one CMUT cell 10 in the dummy chip closer to a plurality of CMUT cells 10 in which bias correction is performed. As the estimated value of the thickness t of the vibrating membrane 12 for use in bias correction, there may be used the average value of the measured values or measured values of the vibrating membrane 12 obtained from the dummy chip.

For example, when correcting variation in the thickness t of the vibrating membrane 12 for each wafer lot, at least one of the chips on the same wafer as the CMUT chip in which bias correction is performed is set as a dummy chip, the thickness t of the vibrating membrane 12 of an arbitrary CMUT cell 10 of at least one location of the dummy chip is measured, and the measured value, the average value of the measured values, or the like is set as an estimated value. During measurement, for example, measurement is performed while observing the section of the vibrating membrane 12 of the CMUT cell 10 by a microscope. At this time, it is desirable that a device, such as a scanning electron microscope or a transmission electron microscope, which can perform measurement of a nanometer order, is used as the microscope such that variation in the thickness t of the vibrating membrane 12 can be measured.

Returning to the flowchart of FIG. 6, after the measurement of S102 is performed, the corrected bias voltage is calculated on the basis of the collapse voltage of each CMUT cell 10 and the parameter proportional to the resonance frequency of the vibrating membrane 12 in the ultrasonic transmission and reception direction (S103).

Thereafter, correction data based on the corrected bias voltage to be applied to each CMUT cell 10 is stored in the storage unit 34 (S104).

Then, the corrected bias voltage is applied to each CMUT cell 10 on the basis of the correction data stored in the storage unit 34 (S105). The step of S105 is a step in which the ultrasonic diagnostic device 30 is actually used.

Next, the effect of reducing variation in transmission and reception sensitivity when the bias voltage is corrected on the basis of the invention will be described. FIG. 7 is a comparison table of variation in transmission and reception sensitivity while changing a correction condition of the bias voltage to be applied to each CMUT cell 10.

FIG. 7 shows a result of verification when the gap thickness g and the thickness t of the vibrating membrane 12 vary by ±10% with respect to the design value. The correction condition has three conditions of correction (hereinafter, referred to as correction according to the invention), with the collapse voltage and the resonance frequency of the invention, correction (hereinafter, referred to as no correction) in which the collapse voltage and the resonance frequency are not taken into consideration, and correction (hereinafter, referred to as collapse voltage correction) only by the collapse voltage. While variation in transmission and reception sensitivity is about ±20% and about ±10% in case of no correction and collapse voltage correction, in case of correction according to the invention, variation in transmission and reception sensitivity is about ±5%. That is, with the correction according to the invention, variation in transmission and reception sensitivity can be reduced to about ¼ in case of no correction and ½ when only the collapse voltage is used.

In this way, in the ultrasonic diagnostic device of the invention, since it is possible to reduce variation in transmission and reception sensitivity among a plurality of CMUT cells even if the gap thickness and the thickness t of the vibrating membrane vary, irregularity of an ultrasound image is eliminated, making it possible to provide a higher-quality ultrasound image. In terms of manufacturing using a semiconductor process, it is possible to reduce frequency of variation management. For this reason, it is possible to improve yield of a CMUT chip and to reduce the manufacturing time.

FIG. 8 is a configuration diagram showing an ultrasonic diagnostic device according to another embodiment. In this embodiment, each of transmission and reception sensitivity correction units 45-1 to 45-n corrects a bias voltages to be applied to each of CMUT cells 10-1 to 10-n so as to become a preset value during manufacturing. For this reason, when using an ultrasonic diagnostic device 30d, it is not necessary to control the transmission and reception sensitivity correction units 45-1 to 45-n, and as in the foregoing embodiments, it is not necessary to provide the storage unit 34, the control unit 36, and the external device 41 as constituent elements. The constituent elements excluding the transmission and reception sensitivity correction units 45-1 to 45-n are the same as those in the foregoing embodiments, and thus description thereof will not be repeated.

Figure 9:
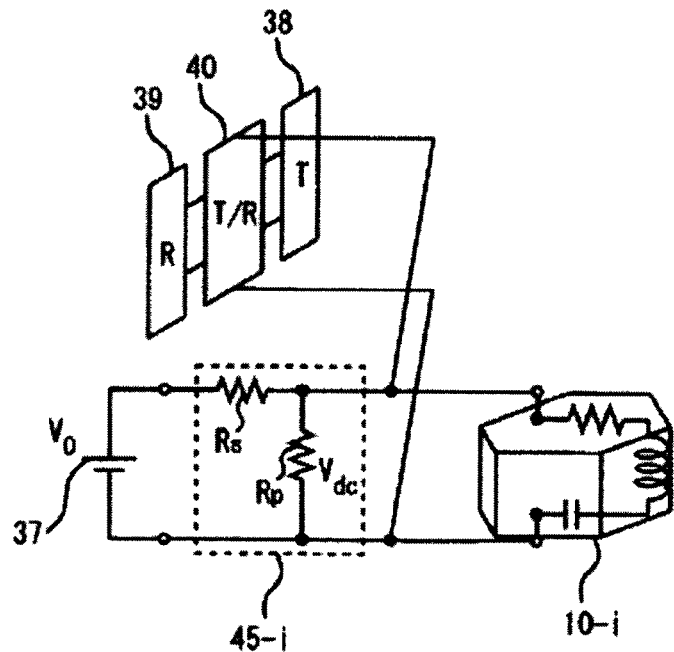
FIG. 9 is a diagram showing an example of a specific configuration of a transmission and reception sensitivity correction unit according to another embodiment.

Next, the specific configuration of the transmission and reception sensitivity correction units 45-1 to 45-n of the ultrasonic diagnostic device 30d according to this embodiment will be described. FIG. 9 is a diagram showing an example of a specific configuration of one transmission and reception sensitivity correction unit 45-i according to this embodiment.

In this embodiment, fixed resistance elements Rp and Rs are disposed as the transmission and reception sensitivity correction unit 45-i in series and in parallel between the CMUT cell 10-i and the bias power source 37, and the bias voltage is divided by the two resistors, thereby correcting the voltage to be applied to the CMUT cell 10-i. Rp and Rs have resistance values which are selected at the time of manufacture of the ultrasonic diagnostic device 30d and embedded. The transmission and reception sensitivity correction units 45-1 to 45-n are not limited to the example shown in FIG. 9 insofar as a plurality of bias voltage values to be output can be selected.

Figure 10:
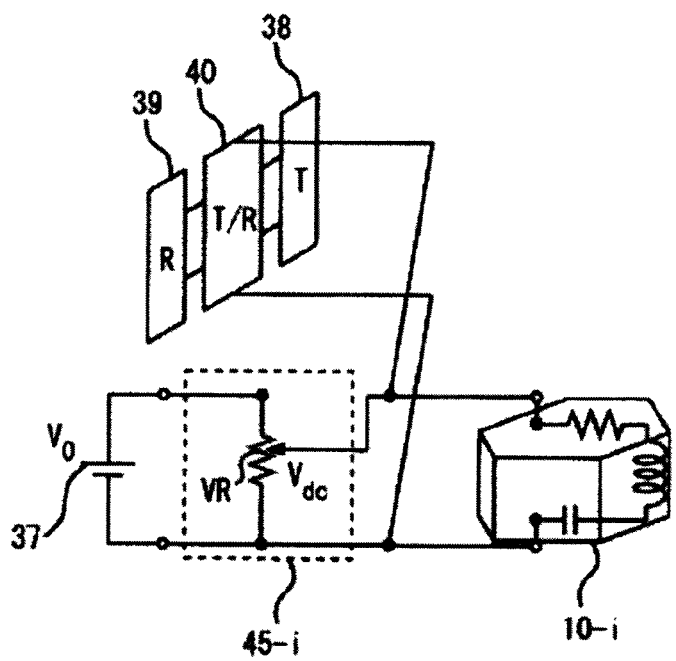
FIG. 10 is a diagram showing another example of a specific configuration of a transmission and reception sensitivity correction unit.

FIG. 10 is a diagram showing another example of a specific configuration of one transmission and reception sensitivity correction unit 45-i according to this embodiment. For example, as shown in FIG. 10, a variable resistor VR may be used, and a resistance value may be set at the time of manufacture, thereby correcting the bias voltage. There may be used a voltage limit circuit having a variable resistor and a Zener diode, a variable resistor and a transistor, or a constant voltage circuit having an operational amplifier. In FIGS. 9 and 10, although an example where one transmission and reception sensitivity correction unit 45-i is provided for one CMUT cell 10-i has been described, as described above, the same corrected bias voltage may be applied to a plurality of CMUT cells.

Figure 11:
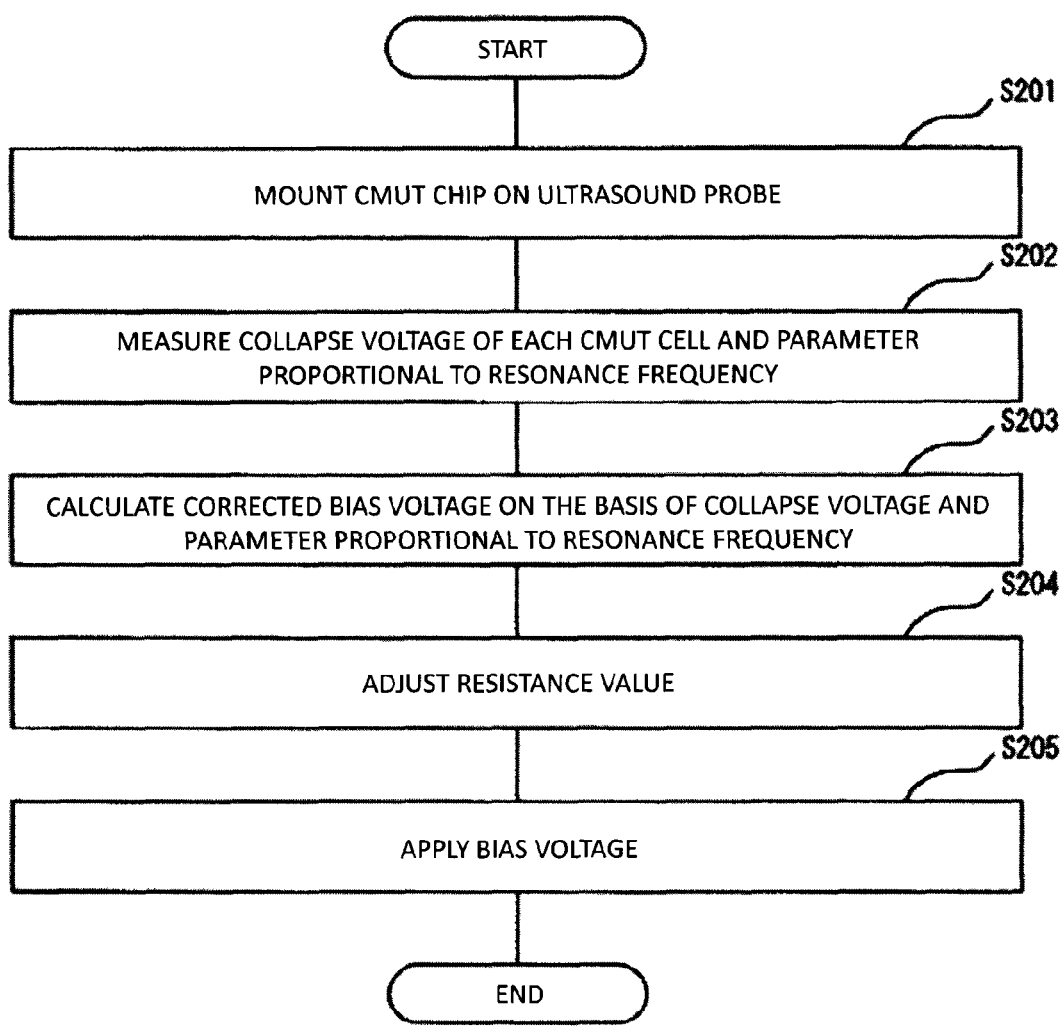
FIG. 11 is a flowchart showing a procedure of transmission and reception sensitivity correction according to another embodiment.

Next, a procedure of transmission and reception sensitivity correction of the CMUT cell 10 according to this embodiment will be described. FIG. 11 is a flowchart showing a procedure of transmission and reception sensitivity correction according to this embodiment.

First, a CMUT chip is mounted on the ultrasound probe 31 (S201).

Then, the collapse voltage of each CMUT cell 10 and a parameter proportional to the resonance frequency of the vibrating membrane 12 in the ultrasonic transmission and reception direction are measured (S202).

After the measurement of S202 is performed, a corrected bias voltage is calculated on the basis of the collapse voltage of each CMUT cell 10 and the parameter proportional to the resonance frequency of the vibrating membrane 12 in the ultrasonic transmission and reception direction (S203).

Thereafter, the resistance values of the transmission and reception sensitivity correction units 45-1 to 45-n are adjusted (S204). Then, the bias voltage is applied to each CMUT cell 10 (S205).

In this embodiment, although S204 as a step of adjusting the resistance values in advance at the time of manufacture of the ultrasonic diagnostic device 30d is required, in S205 of applying the bias voltage, a fixed bias voltage is merely applied to each of the transmission and reception sensitivity correction units 45-1 to 45-n, whereby the corrected bias voltage which is separately controlled can be applied to each CMUT cell 10. The fixed bias voltage which is applied to each of the transmission and reception sensitivity correction units 45-1 to 45-n may be variable temporally.

In the ultrasonic diagnostic device according to this embodiment, as in the foregoing embodiments, since it is possible to reduce variation in transmission and reception sensitivity among a plurality of CMUT cells even if the gap thickness and the thickness t of the vibrating membrane vary, irregularity of an ultrasound image is eliminated, making it possible to provide a higher-quality ultrasound image.

Although the preferred embodiment of the ultrasonic diagnostic device and the ultrasound probe according to the invention has been described by reference to the accompanying drawings, the invention is not limited to this example. It is obvious to those skilled in the art that various alteration examples or correction examples may be made within the scope without departing from the technical spirit disclosed in this application, and it is understood that these still fall within the technical scope of the invention.

REFERENCE SIGNS LIST

10: CMUT cell, 11: upper electrode, 12: vibrating membrane, 14: lower electrode, 16: substrate, 17: void, 18: support portion, 19: bias power source, 20: AC power source, 30: ultrasonic diagnostic device, 31: ultrasound probe, 32: ultrasonic diagnostic device body, 34: storage unit, 35-1 to 35-*n*: transmission and reception sensitivity correction unit, 36: control unit, 37: bias power source, 38: transmission unit, 39: reception unit, 40: transmission and reception separation unit, 41: external device, 42: image processing unit, 43: D/A converter, 45-1 to 45-*n*: transmission and reception sensitivity correction unit, 47: input unit, 48: display unit

The invention claimed is:

1. An ultrasonic diagnostic device comprising:
   an ultrasound probe which transmits an ultrasonic wave to an object and receives a reflected wave from the object;
   a transmission unit which transmits the ultrasonic wave;
   a reception unit which receives the reflected wave from the object;
   a control unit which controls the transmission unit and the reception unit; and
   a bias power source which supplies a bias voltage to the ultrasound probe,
   wherein the ultrasound probe includes a plurality of CMUT cells each having an upper electrode and a lower electrode which are disposed opposite to each other to apply the bias voltage, and a vibrating membrane which is disposed between the upper electrode and the lower electrode and vibrates during transmission and reception, and
   a transmission and reception sensitivity correction unit which corrects the bias voltage supplied from the bias power source on the basis of correction data for correcting the bias voltage applied to the upper electrode and the lower electrode and supplies the corrected bias voltage to the upper electrode and the lower electrode, and
   the correction data is calculated using at least one parameter selected from the thickness of the vibrating membrane and the resonance frequency of the vibrating membrane.

2. The ultrasonic diagnostic device according to claim 1, wherein the correction data is calculated using the resonance frequency and a collapse voltage of each of the CMUT cells.

3. The ultrasonic diagnostic device according to claim 2, wherein the correction data is calculated using a value proportional to the absolute value of the difference between a reference frequency, which cancels the dimension of the resonance frequency, and the resonance frequency.

4. The ultrasonic diagnostic device according to claim 1, wherein, when the resonance frequency is f, the collapse voltage of each of the CMUT cells is $V_c$, and the value of β as a real number is set within a range of 0<β<3, the correction data is calculated using a value proportional to $V_c \cdot f^{-\beta}$ as the bias voltage applied to each of the CMUT cells.

5. The ultrasonic diagnostic device according to claim 1, wherein the correction data is calculated using the thickness of the vibrating membrane of each of the CMUT cells and a collapse voltage of each of the CMUT cells.

6. The ultrasonic diagnostic device according to claim 5, wherein the correction data is calculated using a value proportional to the absolute value of the difference between a reference thickness, which cancels the dimension of the thickness of the vibrating membrane of each of the CMUT cells, and the thickness.

7. The ultrasonic diagnostic device according to claim 1, wherein, when the thickness of the vibrating membrane of each of the CMUT cells is t, a collapse voltage of each of the CMUT cells is $V_c$, and the value of β as a real number is set within a range of 0<β<3, the correction data is calculated using a value proportional to $V_c \cdot t^{-\beta}$ as the bias voltage applied to each of the CMUT cells.

8. The ultrasonic diagnostic device according to claim 1, wherein the transmission and reception sensitivity correction unit is provided for each CMUT cell.

9. The ultrasonic diagnostic device according to claim 1, wherein the transmission and reception sensitivity correction unit is provided for every two or more CMUT cells.

10. The ultrasonic diagnostic device according to claim 1, wherein the transmission and reception sensitivity correction unit is provided for each ultrasound probe.

11. An ultrasound probe comprising:
    a plurality of CMUT cells each having an upper electrode and a lower electrode which are disposed opposite to each other to apply a bias voltage, and a vibrating membrane which is disposed between the upper electrode and the lower electrode and vibrates during transmission and reception; and
    a transmission and reception sensitivity correction unit which corrects the bias voltage on the basis of correction data calculated using at least one parameter selected from the thickness of the vibrating membrane and the resonance frequency of the vibrating membrane.

12. The ultrasound probe according to claim 11, wherein the correction data is calculated using the resonance frequency and a collapse voltage of each of the CMUT cells.

13. The ultrasound probe according to claim 11, wherein, when the resonance frequency is f, the collapse voltage of each of the CMUT cells is $V_c$, and the value of β as a real number is set within a range of 0<β<3, the correction data is calculated using a value proportional to $V_c \cdot f^{-\beta}$ as the bias voltage applied to each of the CMUT cells.

14. The ultrasound probe according to claim 11, wherein the correction data is calculated using the thickness of the vibrating membrane of each of the CMUT cells and a collapse voltage of each of the CMUT cells.

15. The ultrasound probe according to claim 11, wherein, when the thickness of the vibrating membrane of each of the CMUT cells is t, a collapse voltage of each of the CMUT cells is $V_c$, and the value of β as a real number is set within a range of 0<β<3, the correction data is calculated using a value proportional to $V_c \cdot t^{-\beta}$ as the bias voltage applied to each of the CMUT cells.

* * * * *